United States Patent [19]
Parker et al.

[11] Patent Number: 5,334,538
[45] Date of Patent: Aug. 2, 1994

[54] GOLD SOL IMMUNOASSAY SYSTEM AND DEVICE

[75] Inventors: James E. Parker, Long Beach; Aileen Herranen, Woodland Hills, both of Calif.

[73] Assignee: V-Tech, Inc., Pomona, Calif.

[21] Appl. No.: 818,341

[22] Filed: Jan. 9, 1992

Related U.S. Application Data

[63] Continuation of Ser. No. 617,608, Nov. 26, 1990, abandoned.

[51] Int. Cl.⁵ .................................................. G01N 33/553
[52] U.S. Cl. ........................................ 436/525; 422/55; 422/56; 422/57; 422/58; 422/101; 422/102; 436/164; 436/165; 436/169; 436/518; 436/805; 436/807; 436/810
[58] Field of Search .................................. 422/55–58, 422/61, 101, 102; 436/518, 525, 805, 807–810, 164, 165, 169

[56] References Cited

U.S. PATENT DOCUMENTS

| | | | |
|---|---|---|---|
| 4,313,734 | 2/1982 | Leuvering | 422/61 |
| 4,780,285 | 10/1988 | Kuypers et al. | 422/58 |
| 4,912,034 | 3/1990 | Kalra et al. | 422/58 |
| 4,965,187 | 10/1990 | Tonelli | 422/102 |
| 4,999,163 | 3/1991 | Lennon et al. | 422/58 |
| 5,006,464 | 4/1991 | Chu et al. | 422/58 |

FOREIGN PATENT DOCUMENTS 2204398 11/1988 United Kingdom ............... 435/970

*Primary Examiner*—Toni R. Scheiner
*Assistant Examiner*—Christopher L. Chin
*Attorney, Agent, or Firm*—I. Morley Drucker

[57] ABSTRACT

A new apparatus and method for immunoassays. A gold sol bead is held in a funnel member. First antibodies are associated with the gold sol bead. When the sample contacts the gold sol it dissolves the bead. A second antibody is impregnated on an immunosorbent surface. When the dissolved gold sol passes this surface, any antigen already reacted with the first antibody present reacts with the second antibody forming a gold: first antibody: antigen: second antibody: immunosorbent complex. The gold sol acts as the visible label.

13 Claims, 1 Drawing Sheet

5,334,538

GOLD SOL IMMUNOASSAY SYSTEM AND DEVICE

CROSS REFERENCE TO RELATED APPLICATIONS

This application is a continuation of U.S. application Ser. No. 07/617,608, filed Nov. 26, 1990, which is now abandoned.

BACKGROUND OF THE INVENTION

1. Field of the Invention

This invention relates to devices and methods for performing immunotesting, particularly devices and methods of immunotesting having no more than one step.

2. Relevant Art

There are numerous devices and procedures for testing various biological and medical conditions using immunotesting. Many devices use what will herein be referred to as sandwich assays: a first antibody to the antigen is bound to a solid support; the antigen binds to the first antibody, thereby anchoring itself; and finally a second labeled antibody to the same antigen is passed over the anchoring site, thereby placing a label everywhere an anchored antigen presents itself. The antibody: antigen: antibody complex is the "sandwich".

Most conventional tests require at least two steps:
a) contacting the first antibody with the antigen; and
b) contacting the anchored antigen with the labeled antibody.

Usually other steps are also required, developing the label, washing and the like. Each step provides an opportunity for error to arise, thereby affecting the result. The usual errors caused by the operator are preparing the different regents in the wrong concentration, and contacting the regents with the sample and each other in the wrong order. It would be clearly advantageous to have a test that reduced the number of steps required. This is especially advantageous if the user is not trained in medical techniques, like, for instance, retail consumers. One-step tests would be especially advantageous.

SUMMARY OF THE INVENTION

This invention provides a new apparatus and method for immunoassays. A metallic sol (micro particulate metal with attached antibodies) bead or other prelabeled lyophilized immunoreactive reagent is held in a funnel member. A first immunosorbent is associated with the labeled immunoactive reagent bead forming a labeled immunosorbent complex. When the sample contacts the lyophilized bead it dissolves the bead. A second immunosorbent has been impregnated on an immunosorbent surface. When the dissolved immunosorbent complex passes this surface, any analyte already reacted with the first immunosorbent present reacts with the second immunosorbent forming a labeled immunoactive reagent: first immunosorbent: antigen: second immunosorbent: complex. The labeled immunosorbent complex acts as the visible label. It is preferred that the labeled immunoactive reagent be metallic sol, particularly a gold sol.

An aspect of this invention is a system for one step immunotesting comprising:
a funnel member having;
a top liquid entrance and a bottom liquid exit;
a cover having pipette access secured to the funnel body across the liquid entrance;
a filter secured to the funnel body across the bottom liquid exit;
a lyophilized bead within the funnel body, between the cap and the filter, and
an immunosorbent member having;
a body member having a means for removable receiving and supporting the bottom end of the funnel; and
an immunosorbent means secured to the body member below the means for receiving and supporting the bottom end of the funnel.

A further aspect of this invention is a funnel member for one-step immunotesting comprising:
a top liquid entrance and a bottom liquid exit;
a cover having pipette access secured to the funnel body across the liquid entrance;
a filter secured to the funnel body across the bottom of the liquid exit; and
a gold sol bead within the funnel body, between the cap and the filter.

DETAILED DISCLOSURE

Figure 1:
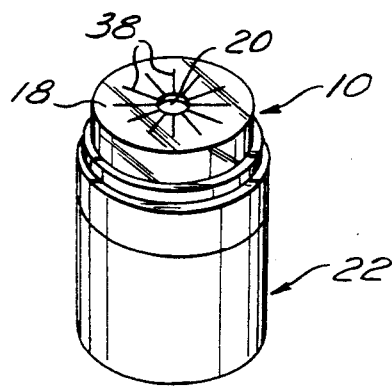
FIG. 1 is a perspective view of the assembled funnel and body member of this invention.

Referring to FIG. 1, the assembled apparatus includes a funnel member 10 and an immunosorbent assembly 22. A cap 18 has an aperture 20 with radiating slits 38. The labeled immunosorbent having a first immunosorbent component having activity for an immunoactive analyte is under the cap 18.

Figure 2:
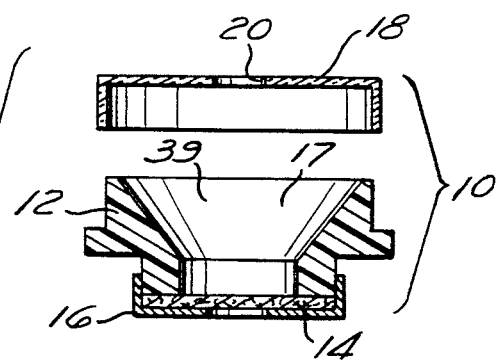
FIG. 2 is a cross sectional view of the apparatus of this invention.

Referring to FIG. 2, a funnel member 10 for a labeled immunoactive reagent bead has a funnel body member 12 which connects with a cover 18 which covers the top liquid entrance 17. The funnel body has a bottom liquid exit covered by a filter 14. The filter 14 is secured to the funnel body by a retaining ring 16. The cover 18 and the retaining ring 16 are snugly press fitted to the funnel body 12 and are not normally removable by the user.

In use the assembled funnel member 10 is removably received by the immunosorbent assembly 22. An immunosorbent body member 24 supports the immunosorbent membrane 26 on top of an absorbent mass 30. The immunosorbent membrane 26 is secured to the body member by a immunosorbent retaining member 28 which is snap fit onto the immunosorbent body 24. The retaining ring 16 of assembled funnel member 10 is received by the top opening 36 of the immunosorbent retaining ring.

Figure 3:
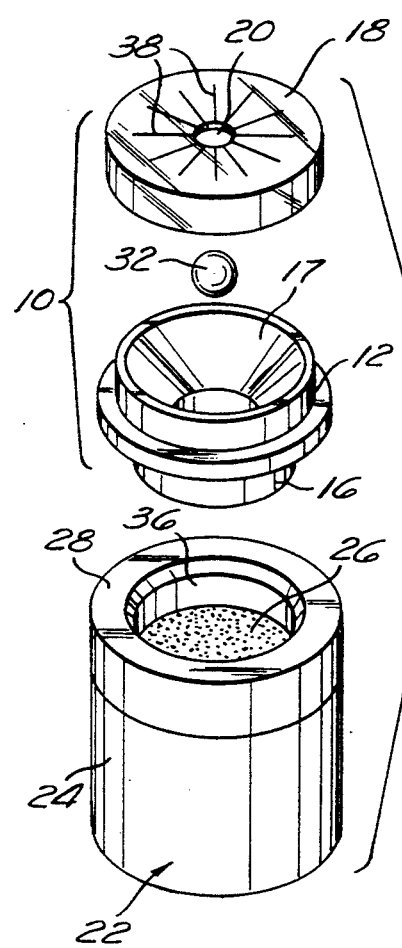
FIG. 3 is a perspective view of the components of the apparatus of this invention.

Referring now to FIG. 3, the immunosorbent system is assembled by inserting a gold sol bead 32 into the internal space 39 (see FIG. 4) formed between the cover 18 and the top of the filter 14 that covers the liquid exit. The cover 18 has an opening 20 for pipette access to the gold sol bead. Radiating slots 38 in the cover provide extra flexibility for insertion of a pipette, while allowing the cover to retain enough structural integrity to prevent the gold sol bead 32 from accidental removal from the internal space 38. The funnel member fits snugly but removably into the top opening 36 of the immunosorbent support member. The immunoactive components are disposed on the surface of the immunosorbent membrane 26.

Figure 4:
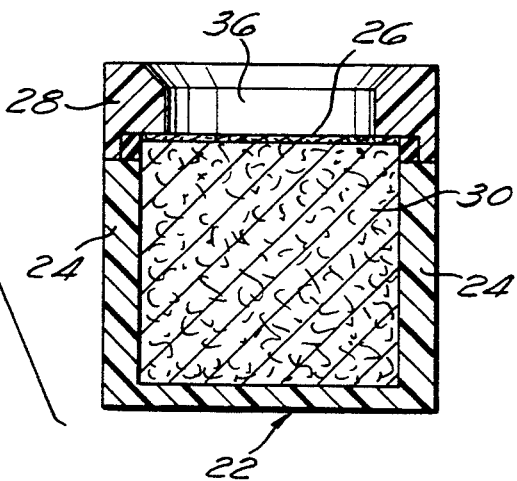
FIG. 4 is a cross sectioned view of the assembled immunoassay funnel of this invention.
Figure 4:
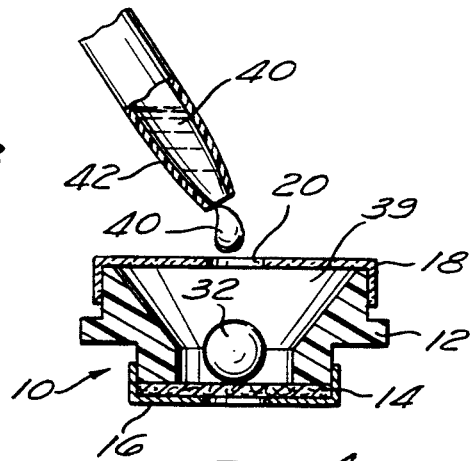

Referring to FIG. 4, the gold sol bead 32 is retained between the cover 18 and the filter member 14. Although the gold sol bead 32 is free to move within the internal space 38, it cannot be removed in normal operation. The sample 40 is added by pipette 42 through the opening 20.

The funnel provides a means for containing a labeled immunosorbent having a first immunosorbent having activity for the immunoactive analyte. The funnel is liquid sample receivable, by pipette or other conventional means, and is liquid flowable, in the sense that the liquid sample flows freely from the labeled immunosorbent chamber.

Although the structural components of this invention could be made of any suitable structural material, plastic is preferred. For example, high density polystyrene can be used for body members and retaining rings and polyethylene can be used for cover member. It is preferred that the materials used for the cover be substantially transparent. Then the user can see the gold sol dissolve. The device of this invention is currently envisioned to be readily disposable, but reusable devices could readily be made by use of the appropriate materials.

The filter material 14 can be any material conventionally used for filters. For example, paper, fiber glass, woven fibers such as cotton or nylon, or other similar materials can be used. The choice of the appropriate filter can be important because it can control flow rate and the amount of particulate matter that pass through to the immunosorbent member. In the case of sensitive tests it is usually desirable to allow the sample to pass slowly over the immunosorbent membrane to allow complete antibody: antigen reactions. Depending on the precise flow and filtration characteristics desired, several layers of different filter materials can be used.

The immunosorbent membrane 26 is impregnated with an antibody to the antigen being sought. The antibody is usually chemically attached to the membrane. Any conventional membrane can be used, for example, nylon.

The absorbent material 30 can be any of a number of conventional liquid absorbents. It can be a monolithic solid mass of cellulose acetate, cellulose, Porex®(a solid porous plastic material), or the like, molded to fit the interior of the immunosorbent body member 24, or it can be granular, for example Cellite ®(diatomaceous earth), Drierite ®(anhydrous calcium sulfate), or other solid granular material. The only physical property required is the ability to absorb large amounts of liquid.

The metallic sol bead 32, is made by the process of U.S. Pat. No. 4,313,734. Any of a variety of antibodies can be attached to the metallic particles. It is preferred that a gold sol be used, but platinum, silver, copper, tin, iron, aluminum, chromium, vanadium, arsenic, vanadium, manganese, lead, mercury, barium, titanium, metals, and then oxides, hydroxides, sulfides, halides can be used. (See U.S. Pat. No. 4,314,734) Although metal sols work particularly well in this invention, any labeled immunosorbent, be it antibody or antigen, can be used to form the bead. The primary consideration is that the bead be fairly readily soluble. The label can be visible or even an enzyme. The test can then be used broadly to test for disease or other biological state, or exposure to toxins and other substances. Indeed any molecule, protein, cell wall or membrane, sugar, allergin, or toxin or other molecule or biological material of interest that provokes an immune response in an antibody producing animal, for example, goats, rabbits, or mice can be tested for. Particularly preferred gold sol antibodies are monoclonal antibodies. Particular monoclonal antibodies preferred include those against HCG or pregnancy testing, estrogen, progesterone, testosterone, anabolic steroids, drugs of abuse, for example, morphine, heroin, cocaine, procaine, methadone, fentanyl, cannabin-di-ols and tetra-ols, mescaline, psilocybin, LSD, barbiturates, diazepam, and the like, as well foreign proteins or antibodies produced in response to diseases, for example, AIDS, gonococcus, chlamydia, tuberculosis, the Epstein-Bart virus, and the like.

The presently preferred embodiment, and that which will be described in greater detail is a test for HCG (human chronic gonadotroprin) for detection of pregnancy. Goat poly anti-HCG is placed on the immunosorbent membrane, preferably Gelman Ultrabind 800. Usually a second antibody is also placed on the membrane for test procedure verification.

In use, for example to determine pregnancy, a sample of a biological fluid is taken from a woman suspected of being pregnant. Useful biological fluids include urine, blood serum, and the like measured amount of the fluid sample is contacted with a gold sol bead with in the chamber. Gold sol is very soluble and usually will appear to instantaneously disappear when contacted with the sample. The gold sol reacts with the sample, forming an HCG: labeled antibody complex. The label is microparticulate gold which is complexed with the antibody. The sample drains through the filter at a rate calculated from knowing the affinities of the labelled antibody and the bound antibody with the antigen, and figuring the lowest concentration of antibody that is desired to be detectable. Using typical antibodies for detecting 50 $\mu$IU/ml HCG in serum, the filtration is adjusted to allow about 1 ml to 2 ml of liquid to pass in about five minutes.

If the antigen is present it forms a bound antigen: labeled antibody complex as to flows past the region of bound antibody. A second antibody on the immunosorbent membrane is used to verify that a negative result is valid. The preferred regent is goat or rabbit anti-mouse, immunoglobulin. Since the labeled antibody against HCG is a mouse immunoglobulin, no special labeled antigen need be added to the gold sol bead to achieve the desired result.

In other tests the presence of an antibody in the serum is found by reacting the sample with bead made from the label and an antigen to the antibody tested for. In these tests the agent that provided the immune response is not tested for, but the antibodies produced.

EXAMPLE 1

This example shows how to make the gold sol of this invention.

500 ml of a 0.10 g/1 chloro-auric acid ($HAuCl_4$) solution in distilled water is heated to boiling point in a beaker of 800 ml capacity. 3.5 ml of a 10 g/1 solution of tri-sodium citrate in distilled water is introduced into the boiling solution, after which the gold sol, which has become dark red after an initial blue color, is boiled for a further 15 minutes. After cooling to room temperature, the red gold sol thus obtained is made up to a volume of 500 ml with distilled water in a volumetric flask. The gold sol obtained in this way consists of gold particles with diameters between 45 and 70 nm, as verified by and a light-absorption maximum at 536 nm, while a 536/cm=1.15+/−0.07.

EXAMPLE 2

This example shows how to obtain mouse anti-HCG monoclonal antibody.

A mouse is immunized against HCG by injection with HCG. Its spleen is removed and the spleen cells are hybridized by the standard procedure of Kohler and Milstein (*Nature*, 256, 495 (1975) and *Eur. J. Immunol.*, 6,511 (1976)). Hybridomas are screened by standard techniques to find those that produce antibodies with high affinities for HCG.

EXAMPLE 3

This example shows how to make the gold sol beads of the present invention.

500 ml of the gold sol prepared in the way described as in Example 1 is adjusted to pH 7.0 by means of a solution of 0.01 $NaH_2PO_4$ in 1 liter distilled water. 0.5 ml of a mouse anti-HCG monoclonal antibody solution, with a content of 125 μg antibody per ml, is added dropwise with vigorous stirring to 25 ml of the neutralized gold sol. 0.5 ml of a 50 g/1 fish gelatin (Sigma) in 5 mmol Na Cl/liter in distilled water, which has been adjusted to a pH of 7.0 with a 0.01 mol $NaH_2PO_4$ solution in 1 liter water, is then added, also with stirring.

0.25 ml drops of this solution are dropped into liquid nitrogen. The drops rapidly freeze into substantially spherical beads. A collection of beads is removed and lyophilized, yielding purplish-red, low density, highly soluble, mouse anti-HCG monoclonal beads. These beads are placed in the funnel top of the present invention.

EXAMPLE 4

This example shows preparation of the immunosorbent membrane.

A Gelman ultrabind 800 membrane (a porous polyolefinic material) is impregnated with a lot of polyclonal goat anti-HCG in 0.1 M Citric Acid, 0.2M $NaH_2PO_4$, and 0.9% Nacl. Surrounding the central dot is a ring of polyclonal goat anti-mouse 1qG in 0.1 M Citric Acid, 0.2 M $NaH_2PO_4$, and 0.9 Nacl.

The immunosorbent membrane is placed on the body member as shown in FIGS. 2 and 3.

EXAMPLE 5

This example shows the determination of whether a woman is pregnant. The woman's urine is freshly collected. A 2 ml sample is withdrawn by pipette and placed in contact with the gold sol. The gold sol bead is seen to instantly dissolve through the transparent cover. The liquid drains through the immunosorbent membrane for three minutes.

After no more liquid is left in the funnel, it is removed. Any indication of a central dot indicates more than about 50 μIU/ml of HCG, which is consistent with a diagnosis of pregnancy. No central dot is consistent with a diagnosis of not pregnant. In both cases a deep purple ring will surround the central dot as a test verification.

What is claimed is:

1. A system for one-step immunotesting of a liquid sample for the presence of a particular analyte, comprising:

a funnel body having;
a top liquid entrance and a bottom liquid exit;
a cover having pipette access secured to the funnel body across the top liquid entrance;
a filter secured to the funnel body across the bottom liquid exit at a bottom end of the funnel body;
a gold sol bead within the funnel body, positioned between the cover and the filter, said gold sol bead comprising a particular first immunosorbent agent which is reactive with said particular analyte, to form a labelled immunosorbent-analyte complex,
wherein said pipette access is an opening large enough for a pipette but smaller than the gold sol bead, and
an immunosorbent assembly having;
a body member having a means for removably receiving and supporting the bottom end of the funnel body; and
an immunosorbent means secured within the body member below the means for receiving and supporting the bottom end of the funnel body, said immunosorbent means having, fixed thereto, a second immunosorbent agent complementary and reactive to said labelled first immunosorbent-analyte complex, such that when the labelled first immunosorbent-analyte complex comes into contact with said second immunosorbent agent, a labelled first immunosorbent-analyte-second immunosorbent complex is formed on said immunosorbent means.

2. The system of claim 1 wherein the first immunosorbent agent of the gold sol bead comprises a first antibody to a predetermined antigen contained in the analyte; and wherein
the second immunosorbent agent is a second antibody reactive to said predetermined antigen.

3. The system of claim 2 wherein the first antibody is a monoclonal antibody.

4. The system of claim 2 wherein the second antibody to the predetermined antigen is a polyclonal antibody.

5. The system of claim 2 wherein the immunosorbent member has a third antibody impregnated in the immunosorbent means as a test verification.

6. The system of claim 5 wherein the third antibody is an antibody to the first antibody.

7. The system of claim 6 wherein the first antibody is a monoclonal antibody.

8. The system of claim 7 wherein the third antibody is anti-mouse-IgG.

9. A funnel body for one-step immunotesting comprising:
a top liquid entrance and a bottom liquid exit;
a cover having pipette access secured to the funnel body across the liquid entrance;
a filter secured to the funnel body across the bottom liquid exit; and
a gold sol bead, which includes binding partners that are specific for an analyte being tested for, within the funnel body, between the cover and the filter, wherein said pipette access is an opening large enough for a pipette but smaller than the gold sol bead.

10. The funnel body of claim 9 wherein the cover is substantially transparent.

11. An apparatus for one-step immunotesting of a liquid sample for the presence of a particular analyte comprising:
a walled container having;

a liquid entrance and a liquid exit for containing therewithin a labelled immunosorbent reagent bead comprising first reagent immunosorbent components having binding affinity for a particular immunoactive analyte, to form a labelled immunosorbent-analyte complex;

a cover having pipette access secured to the walled container across the liquid entrance, wherein said pipette access is smaller than said reagent bead, and a filter secured to the walled container across the liquid exit at a bottom end of the walled container, said labelled immunosorbent reagent bead being positioned between the cover and the filter, and an immunosorbent assembly having;

a body member a means for removably receiving and supporting the bottom end of the walled container; and an immunosorbent member secured within the body member below the means for receiving and supporting the bottom end of the walled container, said immunosorbent member having, fixed thereto, a second immunosorbent reagent complementary and reactive to said labelled immunosorbent-analyte complex, such that when the labelled immunosorbent-analyte complex comes into contact with said second immunosorbent reagent, a labelled immunosorbent-analyte-second immunosorbent complex is formed on said immunosorbent member.

12. The apparatus of claim 11 wherein the first reagent immunosorbent components are antibodies complexed to metallic sols.

13. The apparatus of claim 11 wherein the metallic sols are gold sols.

* * * * *